United States Patent
Zaleski

(10) Patent No.: US 10,685,549 B2
(45) Date of Patent: Jun. 16, 2020

(54) ALARM SETTING DERIVED FROM THE VARIABILITY IN SIGNAL CHARACTERISTICS

(71) Applicant: Capsule Technologies, Inc., Andover, MD (US)

(72) Inventor: John Zaleski, Elkton, MD (US)

(73) Assignee: CAPSULE TECHNOLOGIES, INC., Andover, MA (US)

(*) Notice: Subject to any disclaimer, the term of this patent is extended or adjusted under 35 U.S.C. 154(b) by 0 days.

(21) Appl. No.: 16/437,414

(22) Filed: Jun. 11, 2019

(65) Prior Publication Data

US 2019/0295401 A1 Sep. 26, 2019

Related U.S. Application Data

(63) Continuation-in-part of application No. 16/360,376, filed on Mar. 21, 2019.

(60) Provisional application No. 62/646,052, filed on Mar. 21, 2018.

(51) Int. Cl.
*G08B 21/18* (2006.01)
*A61B 5/00* (2006.01)
*G08B 21/02* (2006.01)
*A61B 5/0464* (2006.01)
*A61B 5/024* (2006.01)

(52) U.S. Cl.
CPC ............ *G08B 21/182* (2013.01); *A61B 5/746* (2013.01); *G08B 21/02* (2013.01); *A61B 5/024* (2013.01); *A61B 5/0464* (2013.01)

(58) Field of Classification Search
CPC ........ G08B 21/182; G08B 21/02; A61B 5/746
See application file for complete search history.

(56) References Cited

U.S. PATENT DOCUMENTS

2007/0221224 A1* 9/2007 Pittman ............ A61M 16/0069
128/204.22

* cited by examiner

*Primary Examiner* — Curtis B Odom
(74) *Attorney, Agent, or Firm* — K&L Gates LLP

(57) ABSTRACT

A method for creating alarm signals based on time-series signal behavior determined from real-time discrete data obtained from a medical device. In one embodiment the method includes identifying patterns in preceding time-series measurement threshold breaches in clinical readings obtained from said medical device when associated with a particular patient, and initiating an alarm signal to a front-line clinician based on the preceding quantity of threshold breaches.

8 Claims, 9 Drawing Sheets
(8 of 9 Drawing Sheet(s) Filed in Color)

ALARM SETTING DERIVED FROM THE VARIABILITY IN SIGNAL CHARACTERISTICS

CROSS REFERENCE TO RELATED APPLICATIONS

This application is a continuation-in-part application and claims priority of U.S. patent application Ser. No. 16/360,376 filed Mar. 21, 2019 which claims priority to U.S. Provisional Application 62/646,052 filed Mar. 21, 2018, each of which is herein incorporated by reference in their entirety.

FIELD OF THE INVENTION

The invention relates generally to a method for creating alarm signals based on signal variability derived from discrete time-series data obtained from a medical device and more specifically, to reducing the number false alarms indicating threshold breaches in clinical readings obtained from the medical device.

BACKGROUND

Many electronic documentation systems in acute care settings of healthcare enterprises employ a user interface for documenting clinical information such as patient vital signs, infusions, outputs such as blood and urine flow, laboratory values, notes, images, and orders. Some of these documentation systems include the recording of alarm system events intended for real-time intervention when patients are experiencing emergencies. These emergencies often require immediate response as a matter of patient survival.

Historically, medical devices such as physiologic monitors, mechanical ventilators, etc., record live physiologic signals, such as cardiorespiratory measurements including, but not limited to, heart rate, breathing rate, and blood pressure. These devices then provide the data to documentation systems for continuous management of a patient's status.

These medical devices produce alarm signals in addition to the measurement data, and the alarm signals are intended to provide general notice, warning, and crisis-level notice to the clinicians when certain events are deemed to be of an emergent or potentially life-threatening nature. For example, identification of asystole, ventricular tachycardia or fibrillation, high peak pressure, low tidal volume, and cessation of breathing, or apnea, are events that would merit emergency intervention.

Machine-generated alarm signals are often communicated to central monitoring stations separate from the signals provided to clinical documentation systems as these monitoring stations provide for the review of real-time data intended for interventional guidance to the clinician. These central monitoring stations are intended to provide live and real-time oversight of patient physiological measurements for the express purpose of identifying current status of the patient's vital signs, especially the cardiorespiratory parameters.

Alarm signals issued by the medical devices are typically reactive in nature—meaning they are issued after an identified event occurs. Examples of such events are a threshold limit breach in a particular physiological measurement as listed as examples above. These alarm signals are often transmitted to alarm communication systems for remote notification of clinical staff when the clinicians are not immediately present at the point of care. The communication and display of alarm signals generated by medical devices are functions which will be referred to as being provided by an alarm system.

Historically, alarm systems are static in that they: (1) do not permit dynamic manipulation of alarm thresholds in real-time; (2) are limited in that they require alarm thresholds to be set by clinicians; (3) are not capable of being changed remotely; (4) do not have analytical tools to determine alarm thresholds in real time; (5) do not provide an easy and simple way to toggle between alarm thresholds; (6) do not provide the capability to alter or manipulate alarm thresholds based on the frequency of alarms; (7) do not provide the capability to create new types of alarm signals based on the characteristics of the data based on variations in observed signal behavior, nor tailor these new types of alarm signals based on characteristics of the patient; and (8) do not enable the incorporation of external or secondary information that could inform the user as to whether an alarm is actionable clinically or not. Examples of external or secondary information could include indications of the existence of signal artefacts that could invalidate measurements obtained from a sensor, such as calibration issues or sensor disconnects. This lack of flexibility frequently results in alarms being issued that are actionable, but not clinically informative from the perspective of identifying an issue with the patient, but, rather, an issue with the measurements and measuring equipment. Yet, these types of alarms result in the interruption of care when they distract providers unnecessarily, possibly diverting their attention from those patients who express with truly clinically-actionable events.

The implied lack of flexibility associated with the present family of machine-generated alarm signals can translate into a lack of skill in terms of the accuracy with which reactive medical device alarm signals can detect and discriminate between clinically-actionable indications in the patient and artefact-based signals that carry no clinical importance. This latter event is oftentimes referred to as the occurrence of false alarms.

What is needed is a method to reduce the number of false alarms. The present invention provides an approach for addressing this need.

SUMMARY

In one aspect, the present application is directed to a method for creating a notification based on variations detected in time-series signal behavior from a medical device used in the monitoring and therapeutic management of a patient. In one embodiment the method includes the steps of identifying preceding threshold breaches in a patient's clinical readings within a specified time-frame as a marker of an impending future event. The threshold breaches are defined with respect to a control limit as a deviation from common baselines. The time-series measurement signal is represented as an expected value that has a relatively long-period variation which serves as a baseline from which signal variability is assessed. The expected value may be computed in several ways. In one embodiment, the signal baseline is computed using a moving or running average of the signal over a specified duration. In either embodiment, an alarm signal is issued based upon a deviation meeting specific criteria, such as detecting a pre-specified quantity of threshold breaches within a pre-defined duration or time interval over an agreed-to running average period. These signal notifications are, essentially, new alarm signals which are generated with the intention of communicating patient issues to clinical staff. The aggregation of the signal measurements in the manner described above effectively reduces the overall quantity of single measurement threshold breaches to a single notification based upon aggregated signal behavior according to the method described above. Such an approach is representative of alarm annunciation aggregation by identifying patterns of signal annunciation behavior and using these patterns to define a single notification indicative of the pattern detected in the time-series signal obtained from the discrete data issued by the medical device.

In another embodiment, the step of identifying preceding threshold breaches in a patient's clinical readings includes the steps of continuously monitoring the patient and adjusting the thresholds based on the quantity of such breaches that have occurred previously. In this way, the notification to clinical staff can be based on the frequency with which historical threshold breaches occur. The quantity of notifications generated is based upon the number of acceptable threshold breaches above a pre-determined threshold, and may be customized based on the measurements obtained from a specific patient. The benefit of this customization or personalization of alarm signal thresholds based upon specific patient patterns is that alarm signal notifications are tailored to the patient and, are more sensitive to specific patient signal measurement patterns. This modeling represents an aggregation of patterns of alarm signal annunciations, as described in the preceding paragraph.

The generation of notifications uses a method of calculating a signal baseline using a moving or running average over a defined rolling time interval; setting the upper and lower thresholds in response to the running average; determining a breach of the upper or lower thresholds; and calculating changes in the thresholds if the number of breaches of the upper and lower thresholds exceeds a predetermined amount. This method is similar to methodologies used for signal frequency analysis, such as Periodograms or Fourier transforms, but is based purely on the time-series signal behavior without involving transformations of the signal to frequency space.

The notifications issued based on the calculations described qualitatively above are henceforward referred to as instability alerts as they pertain to deviations in the signal from a stable running average.

BRIEF DESCRIPTION OF DRAWINGS

The patent or application file contains at least one drawing executed in color. Copies of this patent or patent application publication with color drawing(s) will be provided by the Office upon request and payment of the necessary fee.

Various features of the embodiments described herein, together with advantages thereof, may be understood in accordance with the following description taken in conjunction with the accompanying drawings as follows.

DETAILED DESCRIPTION

Figure 1:
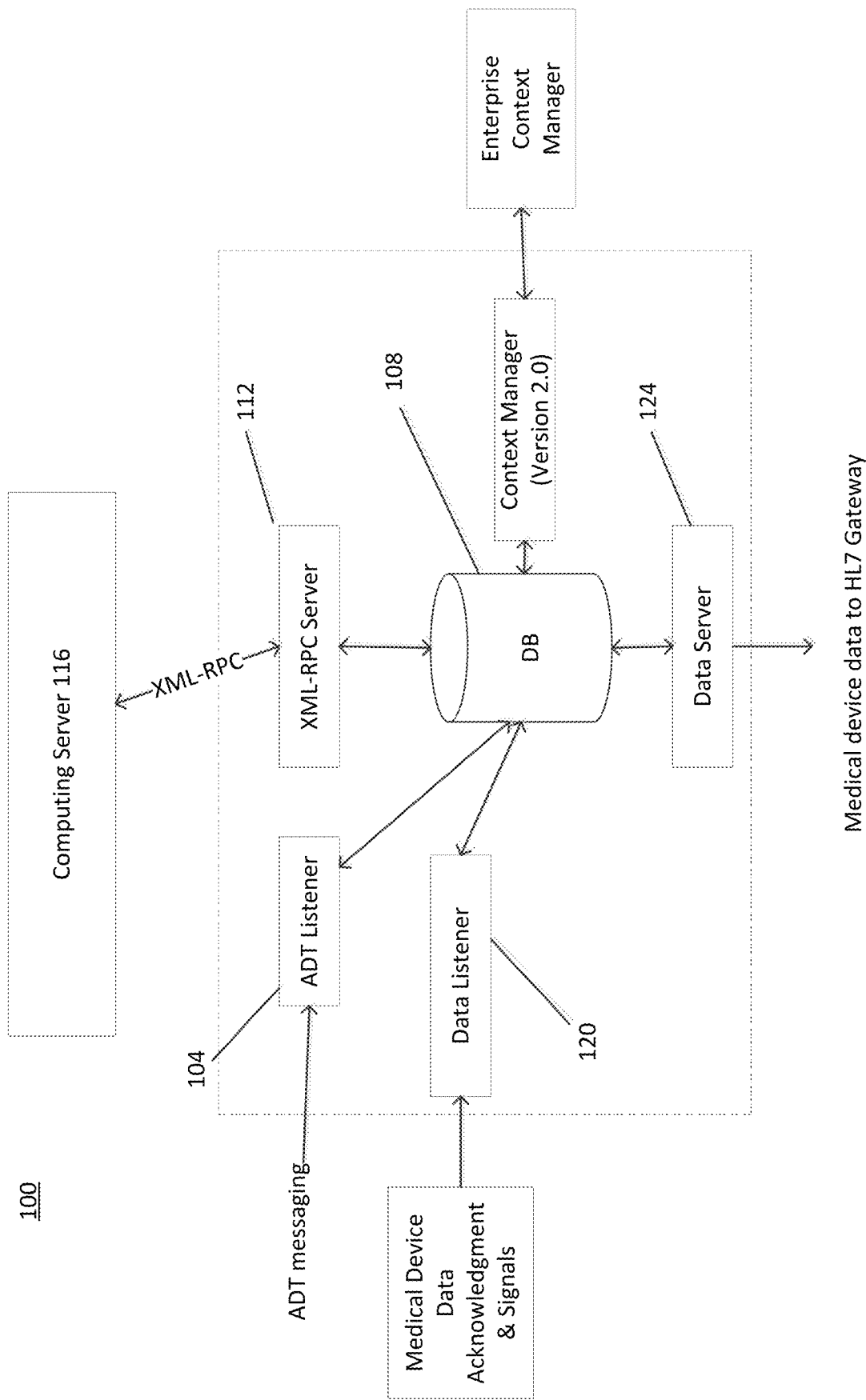
FIG. 1 is a block diagram of an embodiment of a system implementing the method of adjusting signal measurement thresholds associated with the issuing of instability alert notifications.

FIG. 1 is a block diagram of an alarm system for implementing the described method. In one embodiment the system 100 includes an ADT Listener 104 configured to receive patient demographic traffic and populate a database 108, and an XML-RPC Server 112 (as determined by a particular embodiment of the system architecture) configured to communicate data to a user-interface on a server or other computer 116 and generate notifications sent to a user based on the threshold(s) and/or user defined rules. The system also includes a data listener 120 configured to communicate with a system for medical device traffic, and a data server 124 configured to communicate validated data measurements to outbound Health Level Seven (HL7) Interface Engine. One embodiment involves communicating HL7 data through the Bernoulli One System (Bernoulli Enterprise, Inc., Milford, Conn. 06460) to electronic health record systems.

In some embodiments, XML-RPC Server 112 includes a notification tool configured to send a notification to the user when a parameter satisfies a user-defined rule and/or exceeds a threshold value. In various embodiments, computing device 116 can be used any computing device, e.g., a smartphone, tablet PC, laptop computers, etc., configured to display user-interfaces described herein. It should be understood by those of ordinary skill in the art that XML-RPC server 112 and computing device 116 are only examples and that other types of servers and computing devices are further contemplated according to aspects of the present invention. In various embodiments, multiple types of physiologic monitors systems communicate through an HL7 gateway, and traffic is differentiated by patient specific identifiers and location.

A review of the telemetry data from a sampling of patients shows that a trend in increasing signal variability appears to correlate with the telemetry-monitor-issued crisis alarms. The present invention makes use of this increasing variability to herald the onset of telemetry-monitor-issued crisis alarms.

A number of existing methodologies using signal processing exist for evaluating the variability of signals emanating from the patient monitors. These methodologies include Fourier Transforms, Periodograms, etc. These methodologies are successful to varying degrees but an objective of the invention is to create a metric that is relatively simple and employs techniques that were not far-afield within the existing monitoring platforms, such as the Bernoulli One™ platform (Bernoulli Health, CT).

The present invention combines a measurement of signal variation and deviation from a baseline and quantities of such deviations over some defined time interval to generate a signal variability measure. This signal variability measure is termed an "Instability Surveillance Calculation", or ISC, in order to differentiate it from signal variability—such as heart rate variability—which is uniquely defined and understood in the field. Furthermore, the metric ISC can be applied to any signal, not just those associated with heart rate measurement, as is demonstrated herein. The Instability Surveillance Calculation outputs an Instability Alert signal or message that is subsequently transmitted to frontline clinical personnel for action.

In one embodiment, the present invention describes the application of the Instability Alert to detecting heart rate instability, indicating the imminent onset of crisis or warning monitoring alarms issued by a physiologic monitoring system. This embodiment of the Instability Alert, termed heart rate instability, or HRI, alarm derives from variability in signal characteristics determined from the discrete data measurement of heart rate through physiologic monitoring data sampling. In one embodiment, data sampling is obtained from physiologic patient monitors. One such patient monitoring is performed by a General Electric Telemetry Monitor (GE Healthcare, Wauwatosa, Wis., USA, 53226) The discrete data measurement is important as this type of alarm does not derive from the continuously-monitored waveform signal data (i.e., electrocardiogram waveform) but, rather, from the discrete heart rate measurement issued by the physiologic monitor.

Discrete measurements can be taken and issued at various rates. For the purpose of this alarm, the discrete heart rate measurements are issued at the rate of not less than one measurement every two seconds or thirty measurements of heart rate per minute. The discrete data form the basis of two generalized specific characterizations of the discrete signal data from which an alarm annunciation is created.

Figure 2:
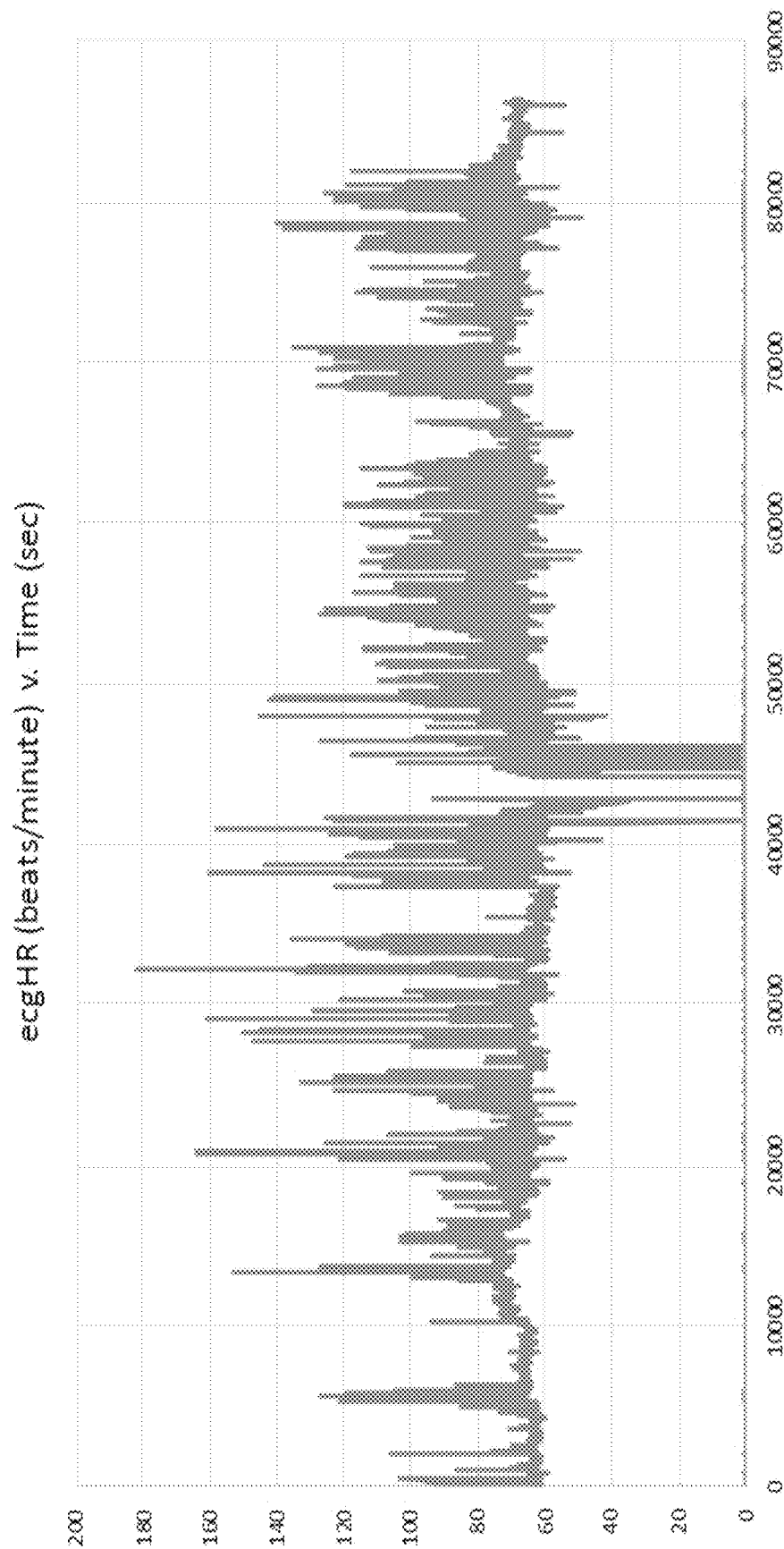
FIG. 2 is a graph of the heart rate of a patient graphed against time.

FIG. 2 is a graph of the heart rate of a patient showing the patient's heart rate graphed against time using two second measurement intervals over a period of about twenty-four hours. It is seen that the heart rate is generally between sixty and eighty beats per minute with a high rate of one hundred and eighty beats per minute and a low rate of zero beats per minute.

Figure 3:
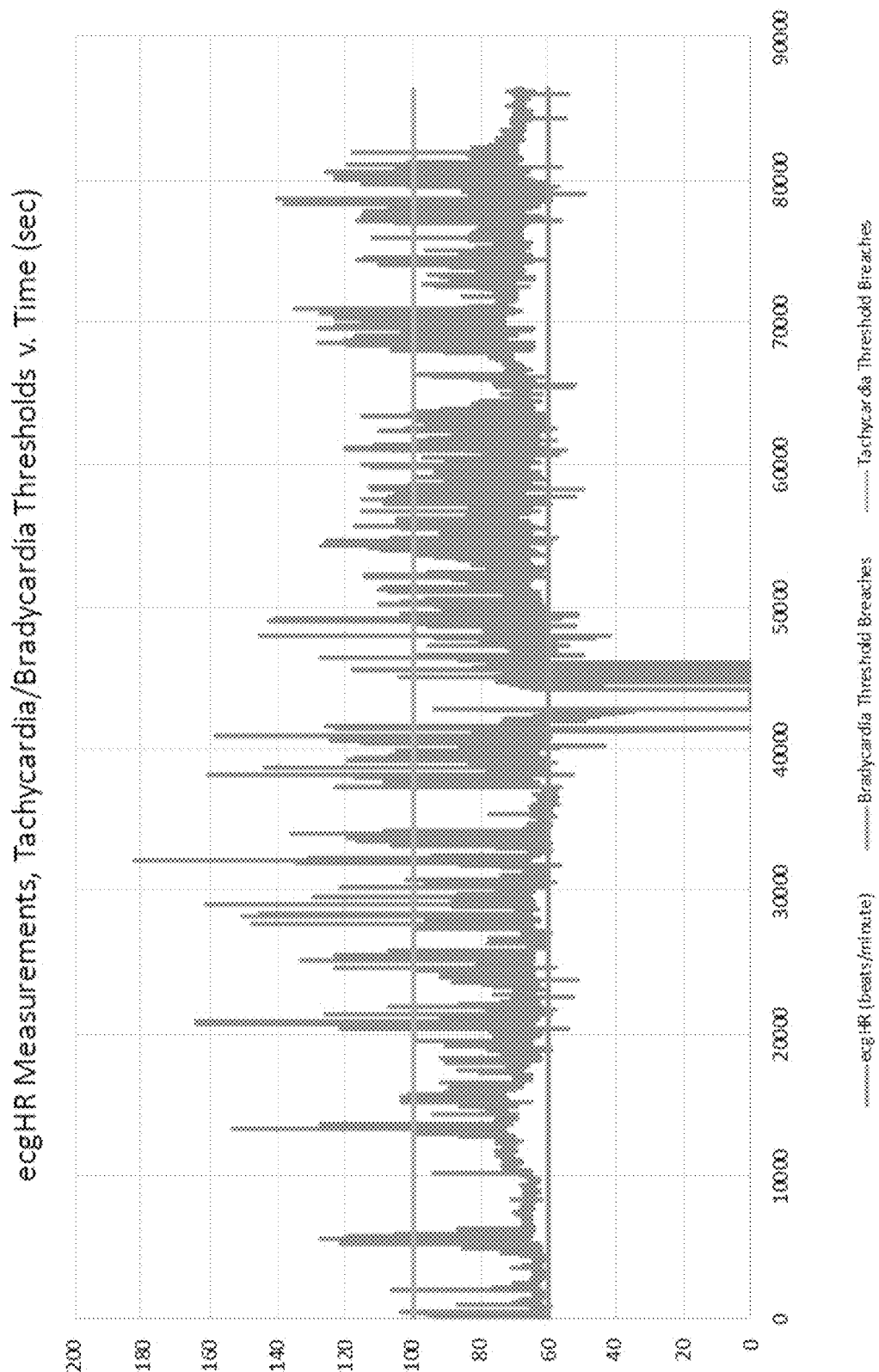
FIG. 3 is the graph of a heart rate of a patient of FIG. 2 upon which are superimposed high and low threshold values, which when exceeded would generate an alarm.

FIG. 3 is the same graph as FIG. 2 but with high and low fixed threshold values, corresponding to low bradycardia (orange) and high tachycardia (gray) threshold limits, corresponding to a sinus range of 60-100 beats-per-minute. It is easily seen through visual inspection of the plot in this figure that there are a large number of two-second heart rate intervals which fall below the bradycardia low threshold limit (1292 times) or above the tachycardia high threshold limit (645 times). Obviously, as the limit thresholds are changed (i.e., moved up or down), then the counts of signal breaches in those limits will change. The counts will vary by patient, by patient condition, by activity level, and on the basis of conditioning and prior medical history. Many variables can and will affect the number of times these thresholds are exceeded. Furthermore, the limit thresholds are according to the general population and may not reflect significance in any given individual patient. It should be noted that many medical devices employ their own specific logic, such as alarm latching, in which an alarm will remain active even if the condition triggering an alarm annunciation is cleared, until the alarm is manually cleared by a user (i.e., care provider). Other logic also provides that certain alarms, if repeated continuously within a pre-determined interval, will not cause subsequent annunciations of the same alarm. These conditions, however, are not addressed here. Rather, the subject of the embodiment addresses the breaching of measured signal thresholds as obtained from the measurement data.

Further, if each of these threshold breaches (a total of breaches) were to trigger an alarm signal notification to an attending clinical provider, responding to the alarms would quickly become extremely draining on the clinical provider particularly because the likelihood that a given threshold breach is truly clinically actionable is very low. Since there are normally many patients being monitored simultaneously one can see that the quantities of threshold breaches can become overwhelming.

Figure 4:
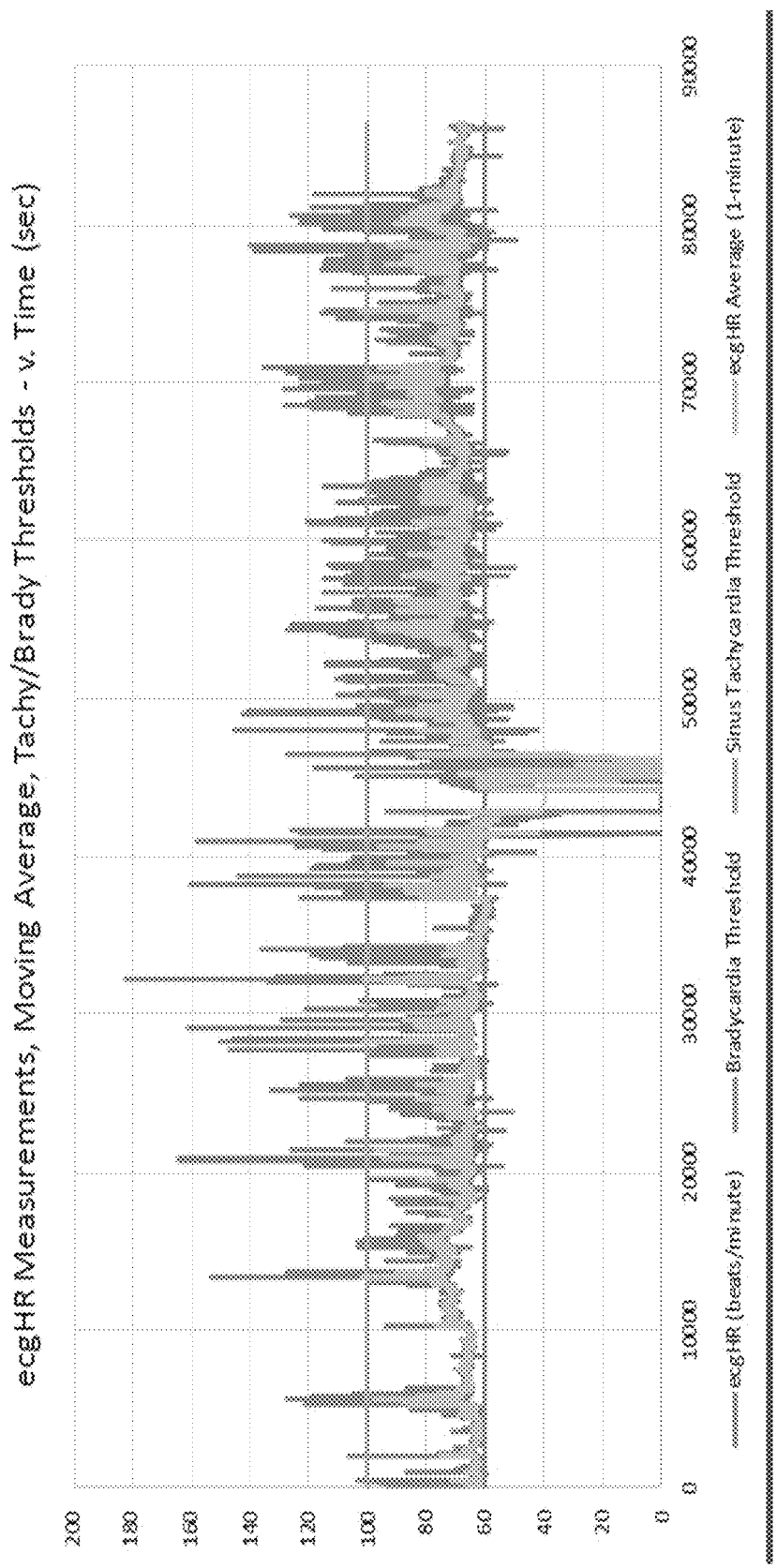
FIG. 4 is a graph of the heart rate measurement signal of FIG. 2 overlaid with a one-minute running average of the heart rate.

To address individual variability in heart rate and hence the setting of threshold values that better reflect physiology of the individual patient, an embodiment of the present invention first takes into account the patient's average heart rate over a defined a sliding window interval. By "smoothing" the signal through temporal moving or running averaging, it is possible to remove a fair amount of "spikey" behavior. In FIG. 4 a one-minute running average is shown in yellow, and the measured signal is shown in blue.

To calculate this moving average the following expression is used:

$$S_{i+N}^{ave} = \frac{1}{N} \sum_{k=i}^{k=i+N} S_k \qquad (1)$$

where:
$S_{i+N}^{ave}$=average heart rate over interval from time i to time i+N;
$S_k$=individual heart rate measurements during interval being averaged, k; in this example, 2-seconds;
N=quantity of data points considered during averaging interval; in this example, thirty measurements; and,
i=index of heart rate during interval containing N heart rate measurements.

The specific averaging interval may be set with clinical consultation at or prior to implementation of the system. This step will involve both clinical and non-clinical participants. Typical values for averaging interval are one-, two-, and five-minutes. In the embodiments disclosed herein, N corresponded to one-minute averaging. This is particularly true when sufficient measurements (30 in this example) are available within a given minute.

Although the heart rate measurements and their average shows a smoothing of the "spikey" behavior there may be significance in the "spikey" signal that is now removed that may have been informative. Counting the threshold breaches with respect to this average heart rate, the lower limit (bradycardia) and upper limit (sinus tachycardia) threshold breach counts are 424 and 730, respectively, for a total of 1,154 threshold breaches. This value is approximately sixty percent the value determined earlier based on bradycardia and tachycardia thresholds alone. Although the sinus tachycardia threshold breaches are greatly reduced, the number is still large when considering that most of these values are not clinically significant.

Further reducing the threshold breaches in the heart rate graph may be accomplished using several approaches.

The first approach is to consider variations in the heart rate values from the average heart rate value, computed above. This is equivalent to looking at the variance or standard deviation of the time-series of heart rates. In one embodiment, instead of looking at the overall time series of heartbeats, the method considers this variation over each averaging interval individually. In the present example discussed above, one-minute segments of the heart rates are used and so the method looks at the variance of the heart rate over each one-minute interval. In one embodiment, rather than computing the variance during each interval under consideration, the method utilizes a fixed interval of variation, whereby the method determines that the heart rate measurements deviate from the running heart rate average by some fixed amount, called a "threshold alert" limit deviation; ($L_{TA}$). The value of this threshold alert limit deviation is a percentage or fraction of the average signal within the measurement interval. The absolute value of deviation is then determined according to equations (2) and (3):

Upper deviation limit at time interval i:

$$S_{Udl_i} = S_{i+N}^{ave} \times (1 + L_{TA}) \quad (2)$$

Lower deviation limit at time interval i:

$$S_{Ldl_i} = S_{i+N}^{ave} \times (1 - L_{TA}) \quad (3)$$

The value of the upper and lower thresholds, utilize a threshold alarm limit deviation ($L_{TA}$) that is derived empirically from a study population of heart rate data. This value has been determined on the basis of a population of patients within a facility, or even within a particular care unit, such as a cardiac telemetry unit. This value is nominally in the range of 10-30%, with higher values having the effect of reducing overall alarm signal annunciations and lower values providing more sensitivity.

Figure 5:
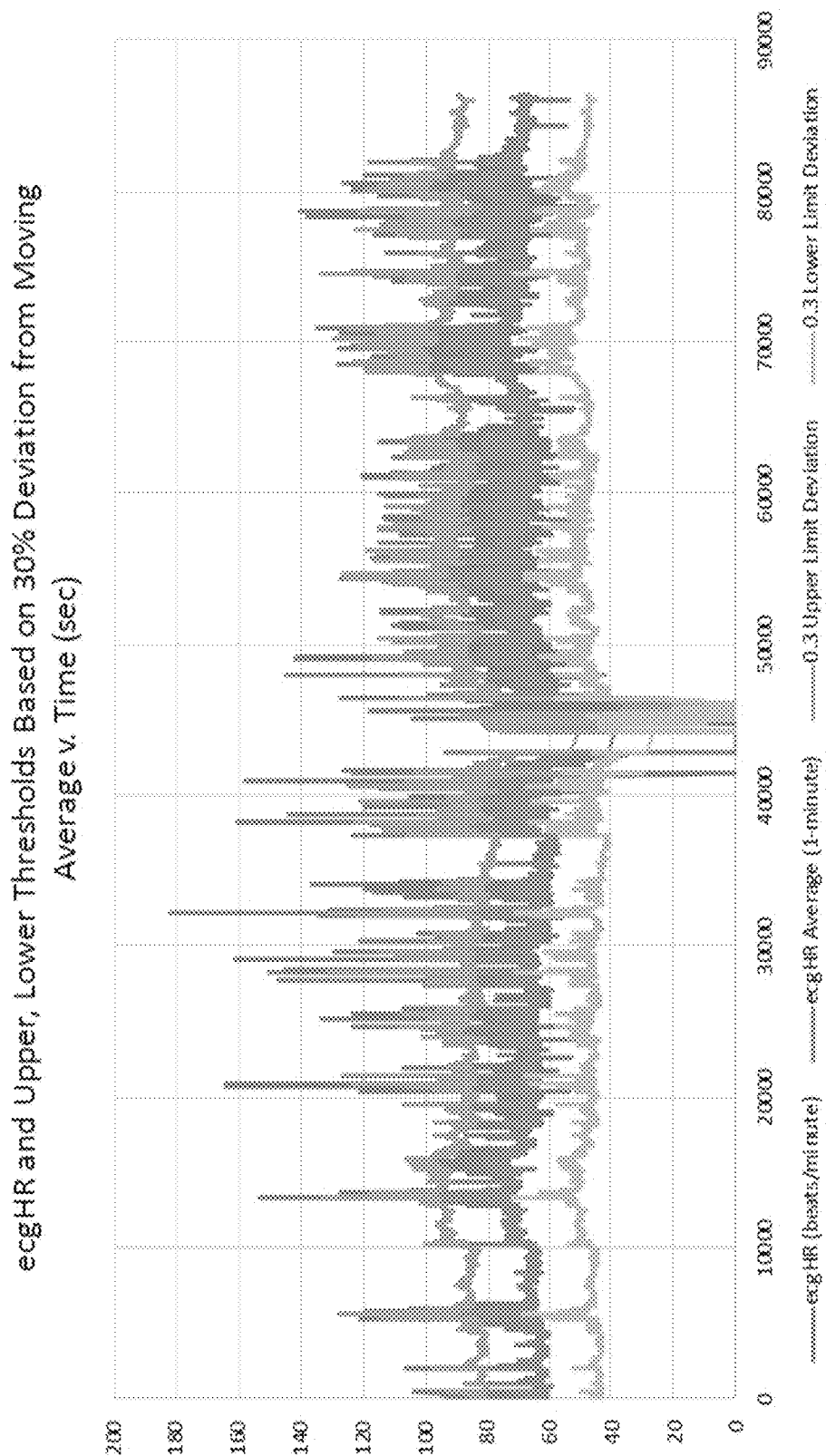
FIG. 5 is a graph of the heart rate measurement of FIG. 4 with a one-minute running average of the heart rate used to set the upper and lower threshold values as 30% of the one-minute running average.

As in the previously discussed fixed thresholds, this level of threshold alarm limit deviation, $L_{TA}$, is also a fixed fraction within a measurement interval. This does not mean, however, that the upper and deviation limits are fixed values—merely that the defining fraction remains unchanged, regardless of the measurements obtained and evaluated. The thresholds therefore move as the average value fluctuates as shown in FIG. 5, which uses a value of 30% of the running average to set the upper and lower limits. This variation is then representative of a normal range of variability associated with the typical measurements of a particular patient.

When the cumulative or total number of threshold breaches is determined for the upper and lower deviation limit for each time window being a fixed percentage of the average, it is not significantly different from the result of using the simple fixed limit threshold assessment discussed previously. In fact, for this heart rate sample, the total counts of the breaches using a fixed threshold and the counts of breaches using thresholds based upon the fixed percentage of the average value of heart rate for a given interval are quite close. In this heart rate sample the count using a percentage of the average heart rate within total measurement interval is 1,154 for $L_{TA}$=30% and the quantity of threshold breaches for fixed bradycardia and tachycardia thresholds are 1,199, as stated previously.

The effect of the use of upper and lower limits that vary with respect to the mean is rather simple. First, consider those instantaneous breaches that deviate beyond the upper and lower calculated limit values as significant. The number of threshold breaches during each averaging window, from i to i+N, in which the measured signal, $S_k$ exceeds or falls below the upper and lower deviation limit is reflected in the plot of FIG. 6, and is computed by accumulating the instances in which:

$$S_k > S_{Udl_i}, \text{ where } k \in Z: k \in [i, N] \quad (4)$$

and $$S_k < S_{Ldl_i}, \text{ where } k \in Z: k \in [i, N] \quad (5)$$

where Z is the total number or sample-set of heart rate measurements. The number of instances (or counts) in which the upper and lower breaches are violated during a given time window from i to i+N are represented by $C_{U_i}$ and $C_{L_i}$, respectively.

When we accumulate the number of breaches over a rolling one-minute interval, we find that the cumulative number of threshold breaches over any one-minute interval (for these data) reaches a peak of 31 at a time of approximately 45,500 seconds. This number of breaches of the thresholds is termed the signal instability. Thus, the larger quantity of signal instability breaches translates into an increased normalized quantity, termed the "Instability Index". The "Instability Index", derived by normalizing the cumulative breaches in Error! Reference source not found. 6, reflects an increasing "cost" associated with measurements that fall outside of the upper or lower deviations limit values and can be considered a distillation of the result of the underlying calculations into a single easy to understand value representation that expresses the degree of variation of the underlying signal.

Figure 7:
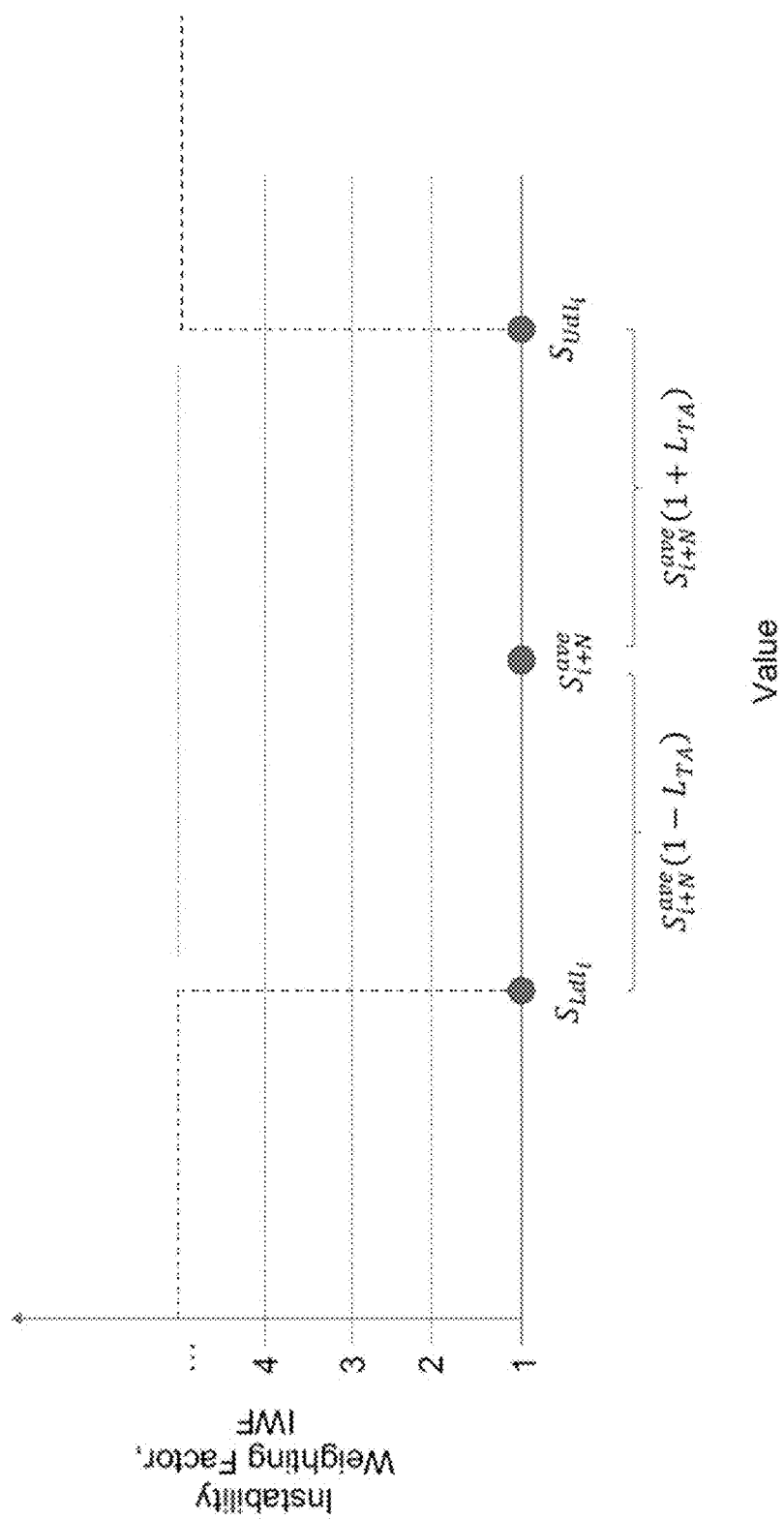
FIG. 7 is a figure depicting the Instability Weighting Factor, IWF, which is used to weight measurements that fall outside of the limits of the upper and lower deviation threshold more heavily than those that are within the limits.

This concept is understood with the aid of FIG. 7. FIG. 7 illustrates the measurement axis along the horizontal line, in which measurement values reside either between or outside the upper and lower deviation thresholds, as defined by the limit fraction and the average signal value. The weight associated with measurements that fall between the ranges of $S_{Ldl_i}$ to $S_{Udl_i}$ are weighted as 1, whereas any measurements that fall outside of this range are weighted in accord with the specific value of "Instability Weighting Factor", IWF; for instance, a value of 5. In other words, the Weighting Factor is a function of the value of the residual between the measurement and the current value of moving average as compared with the upper and lower thresholds. The concept of increasing cost is similar to that of a "gravity well" in that measurements that fall between the upper and lower deviation limits are treated as being within a "normal" range—that is, are allocated an "Instability Weighting Factor", IWF, equal to 1. Yet, any measurements that fall outside the upper and lower deviation limits will be weighted more heavily, thereby increasing the likelihood that they will "stand out" from the other deviations more starkly, thereby differentiate them from other portions of the signal. The weighting magnifies the significance of a measurement outside of a normal range for a specific patient. That is, the farther the measurement is from the moving average, the more significant the measurement is in terms variation, and, hence, should be more likely to result in an alarm.

Figure 8:
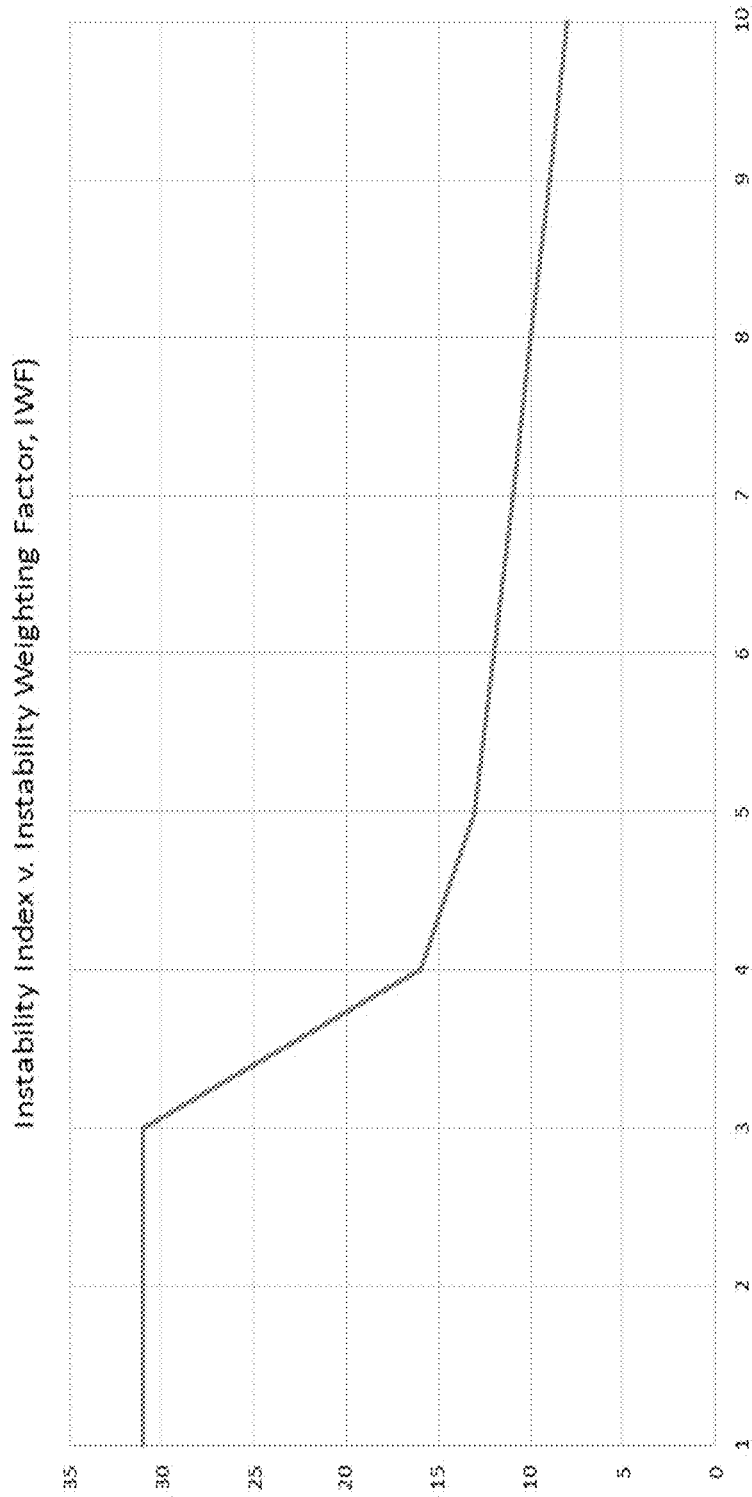
FIG. 8 is the graph of the maximum instability index normalized by IWF, showing how the selection of an optimal value of IWF is obtained.

Selecting the appropriate IWF is somewhat arbitrary but follows a logical approach as indicated with the aid of FIG. 8. FIG. 8 illustrates the effect of the IWF on the computed instability index, calculated according to the expression given by Equation (6), as discussed below. As is shown in the figure, as IWF is increased, the instability index remains initially flat, then drops by approximately 50% at an IWF value of 4, and a further reduction to a value of 13 at an IWF of 5. As IWF is increased further, there is continuing decline of the instability index but not at the rate seen below an IWF value of 5. This value of IWF, by inspection, appears to align with the "knee in the curve". Thus, as an initial default, the IWF is selected to be a value of 5.

The instability index at any averaging interval, i, is computed with the aid of equation (6), in which the "Instability Weighting Factor", IWF, is empirically derived as shown based on the assessment given in the preceding paragraph, and is normally set to a value between 5 and 10 with 5 being the default, which is merely the sum of the high and low breaches normalized by IWF:

$$I_{in_i} = \Sigma_{k=i}^{k=i+N}(C_{U_k} + C_{L_k})/IWF \qquad (6)$$

Equation (6) is merely a normalized sum of the breaches above and breaches below a specific threshold for a specific interval containing N measurements. The normalization factor IWF merely scales the sum of these breaches.

Figure 6:
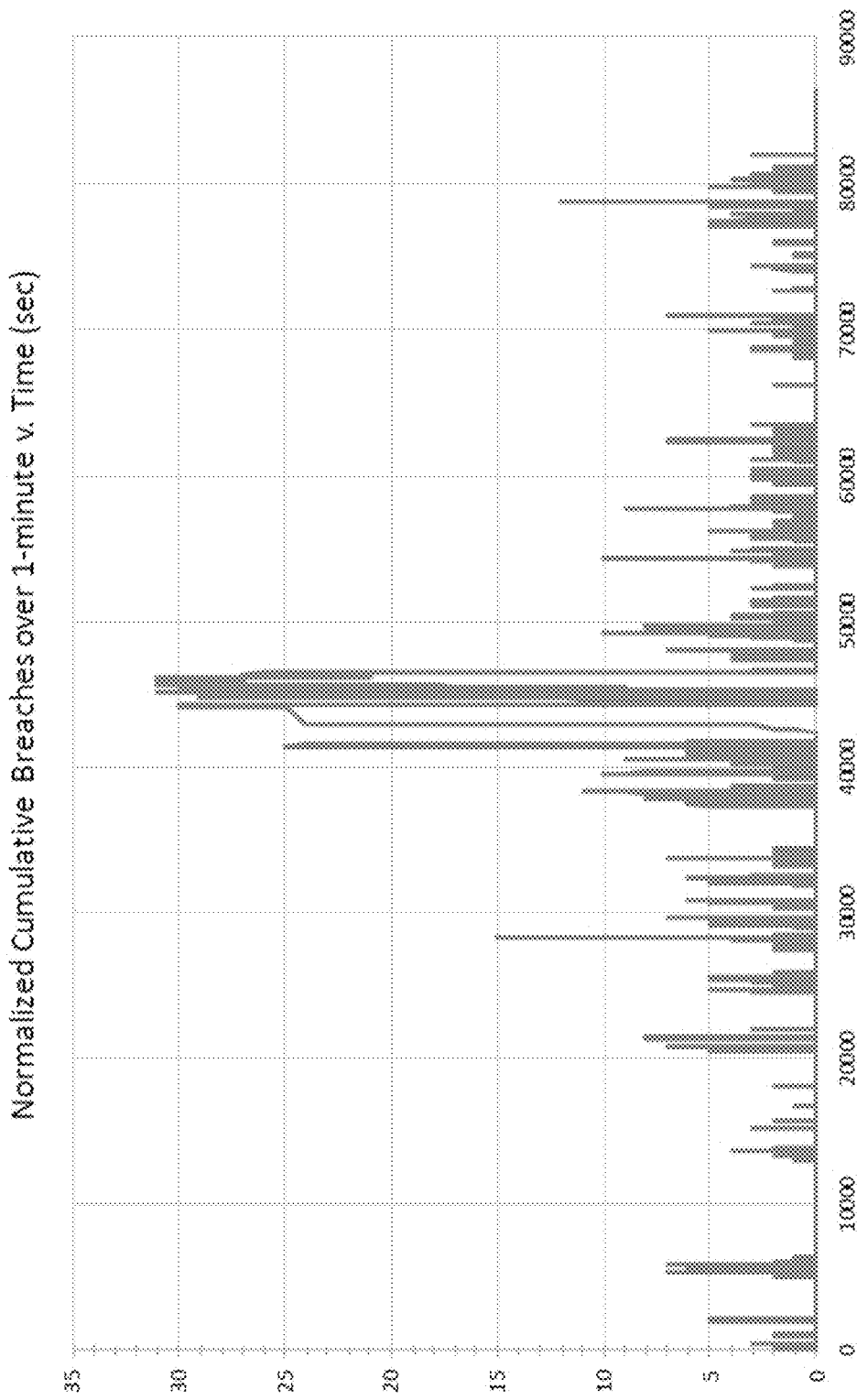
FIG. 6 is a graph of the number of breaches in which the heart rate breached the threshold in an interval set in FIG. 5.
Figure 9:
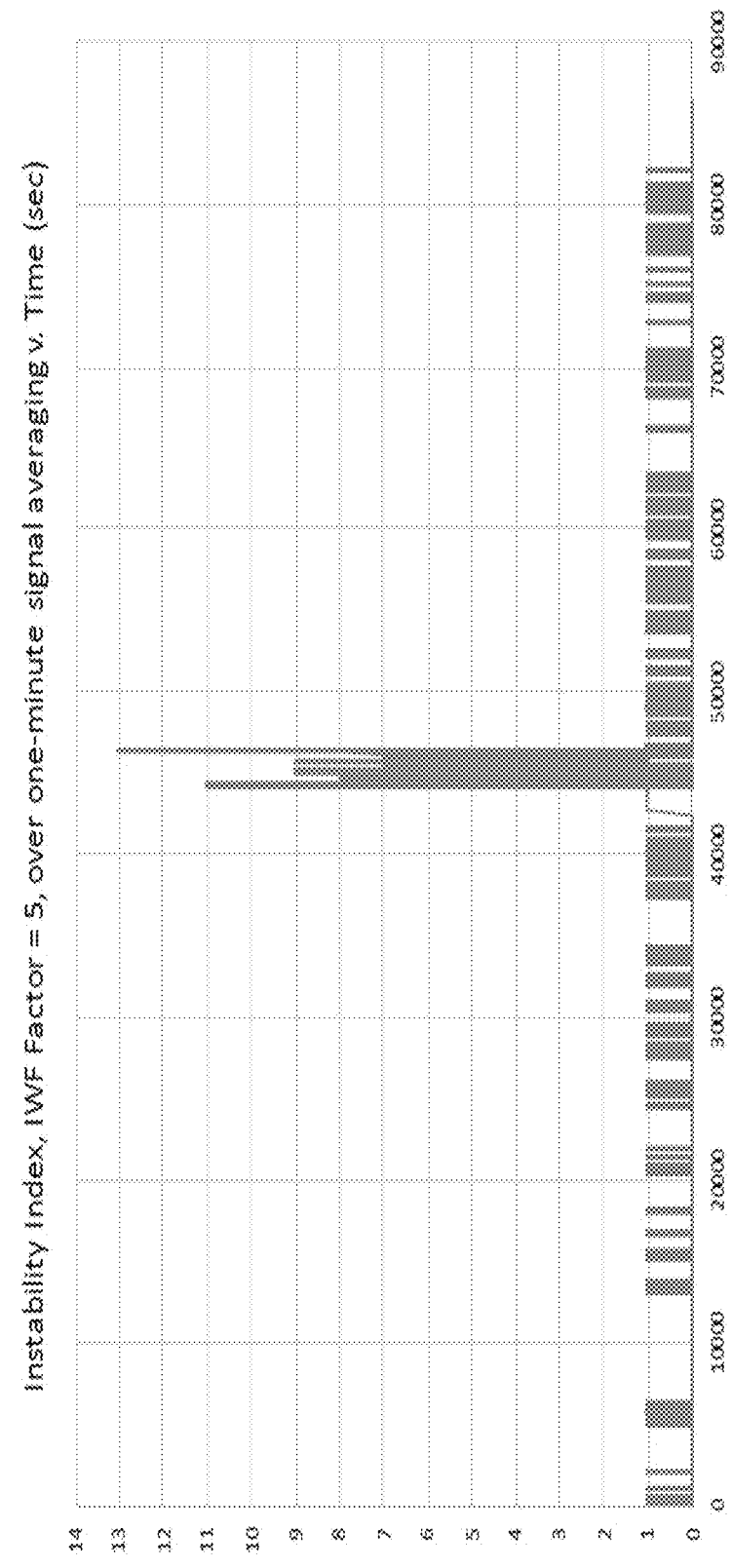
FIG. 9 is the graph of FIG. 6 normalized by an instability factor.

The result is that shown in FIG. 9. Here, the maximum number of instability alerts (i.e., the value of the instability index) does not exceed 13. This value is compared with the value of 31 from FIG. 6 shown previously, or the limit threshold breaches that account for several thousand individual alarms. Thus. a specified threshold value (e.g. 2) may be used as a trigger for alarm annunciation since most of the other counts will not result in annoyance alarms.

The preceding development can be further generalized by treating the IWF as as a step function. In further embodiments, the weight function can be shaped so that its "steep-walled" nature can be made more gradual. That is, as the measurements fall outside of the upper and lower deviation limit, the cost of penalty associated with them increase gradually as a function of "distance" from the upper and lower deviation limit.

Although the method here utilizes one variable, the methods described can be extended from one to multiple dimensions inasmuch as the instability index and underlying calculations can be applied to a vector of measurements (i.e., more than one dimension, such as heart rate, respirations, oxygen saturation, blood pressure, etc.) simultaneously, resulting in an instability index that represents the fusion of multiple variables.

Unless specifically stated otherwise as apparent from the following discussion, it is appreciated that throughout the description, discussions utilizing terms such as "processing" or "computing" or "calculating" or "delaying" or "comparing", "generating" or "determining" or "forwarding or "deferring" "committing" or "interrupting" or "handling" or "receiving" or "buffering" or "allocating" or "displaying" or "flagging" or Boolean logic or other set related operations or the like, refer to the action and processes of a computer system, or electronic device, that manipulates and transforms data represented as physical (electronic) quantities within the computer system's or electronic devices' registers and memories into other data similarly represented as physical quantities within electronic memories or registers or other such information storage, transmission or display devices.

The algorithms presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language, and various embodiments may thus be implemented using a variety of programming languages.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

The examples presented herein are intended to illustrate potential and specific implementations of the present disclosure. The examples are intended primarily for purposes of illustration of the invention for those skilled in the art. No particular aspect or aspects of the examples are necessarily intended to limit the scope of the present invention.

The figures and descriptions of the present invention have been simplified to illustrate elements that are relevant for a clear understanding of the present invention, while eliminating, for purposes of clarity, other elements. Those of ordinary skill in the art may recognize, however, that these sorts of focused discussions would not facilitate a better understanding of the present disclosure, and therefore, a more detailed description of such elements is not provided herein.

The processes associated with the present embodiments may be executed by programmable equipment, such as computers. Software or other sets of instructions that may be employed to cause programmable equipment to execute the processes may be stored in any storage device, such as, for example, a computer system (non-volatile) memory, an optical disk, magnetic tape, or magnetic disk. Furthermore, some of the processes may be programmed when the computer system is manufactured or via a computer-readable memory medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary.

Computer systems and computer-based devices disclosed herein may include memory for storing certain software applications used in obtaining, processing, and communicating information. It can be appreciated that such memory may be internal or external with respect to operation of the disclosed embodiments. The memory may also include any means for storing software, including a hard disk, an optical disk, floppy disk, ROM (read only memory), RAM (random access memory), PROM (programmable ROM), EEPROM (electrically erasable PROM) and/or other computer-readable memory media. In various embodiments, a "host," "engine," "loader," "filter," "platform," or "component" may include various computers or computer systems, or may include a reasonable combination of software, firmware, and/or hardware.

In various embodiments of the present disclosure, a single component may be replaced by multiple components, and multiple components may be replaced by a single component, to perform a given function or functions. Except where such substitution would not be operative to practice embodiments of the present disclosure, such substitution is within the scope of the present disclosure. Any of the servers, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

In general, it may be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present disclosure. Programming languages for computer software and other computer-implemented instructions may be translated into machine language by a compiler or an assembler before execution and/or may be translated directly at run time by an interpreter.

Examples of assembly languages include ARM, MIPS, and x86; examples of high level languages include Ada, C, C++, C#, COBOL, Fortran, Java, Lisp, Matlab, Pascal, Object Pascal, Swift, Visual Basic; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present disclosure based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods, systems, and tools described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity.

Unless otherwise indicated, all numbers expressing lengths, widths, depths, or other dimensions and so forth used in the specification and claims are to be understood in all instances as indicating both the exact values as shown and as being modified by the term "about." As used herein, the term "about" refers to a ±10% variation from the nominal value. Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques. Any specific value may vary by 20%.

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

It will be appreciated by those skilled in the art that various modifications and changes may be made without departing from the scope of the described technology. Such modifications and changes are intended to fall within the scope of the embodiments that are described. It will also be appreciated by those of skill in the art that features included in one embodiment are interchangeable with other embodiments; and that one or more features from a depicted embodiment can be included with other depicted embodiments in any combination. For example, any of the various components described herein and/or depicted in the figures may be combined, interchanged, or excluded from other embodiments.

What is claimed is:

1. A method for creating alarm signals based on time-series signal behavior of real-time discrete clinical data obtained from a medical device continuously monitoring a patient, the method comprising:
    setting upper and lower thresholds in the patient's real-time discrete clinical data;
    identifying breaches of upper and lower thresholds in the patient's real-time discrete clinical data;
    calculating a moving average over a defined time interval in the real-time discrete clinical data;
    setting new upper and lower thresholds within the defined time interval in response to the moving average;
    determining each new breach of the new upper and lower thresholds in subsequent defined time intervals; and
    calculating subsequent changes in the upper and lower thresholds if the number of breaches of the upper and lower thresholds exceeds a predetermined amount.

2. The method of claim 1, further including the step of issuing an alarm in response to the subsequent number of threshold breaches.

3. The method of claim 1 wherein the new upper and lower thresholds in subsequent defined time intervals is in response to a percentage of the moving average, representative of a normal range of variability associated with the typical measurements of a specific patient.

4. The method of claim 3 wherein the percentage is between 10% and 30% inclusive.

5. The method of claim 1 further comprising the step of normalizing the count of the breaches of the upper and lower threshold to generate an instability index.

6. The method of claim 5 further comprising generating a weighting value for each breach of the upper and lower threshold.

7. The method of claim 6 wherein the weighting value is a function of the magnitude of the difference between the measurement resulting in the breach of the upper and lower threshold and the current value of the moving average.

8. The method of claim 6 comprising generating an alarm in response to the number of threshold breaches having a weighting value greater than a specified threshold value.

* * * * *